United States Patent [19]

Phelps, Sr. et al.

[11] Patent Number: 5,027,825
[45] Date of Patent: Jul. 2, 1991

[54] SELF-CONTAINED STETHOSCOPE TRANSMITTER

[76] Inventors: Jerry A. Phelps, Sr., 6013 Innes Trace, Louisville, Ky. 40222; David Y. Phelps, 50 Golden Ball Rd., Weston, Mass. 02193

[21] Appl. No.: 331,264

[22] Filed: Mar. 30, 1989

[51] Int. Cl.⁵ ............................................. A61B 5/02
[52] U.S. Cl. ................................... 128/715; 128/773
[58] Field of Search ................. 128/715, 773, 903; 381/67

[56] References Cited

U.S. PATENT DOCUMENTS

| | | | |
|---|---|---|---|
| 3,171,892 | 3/1965 | Parthe . | |
| 3,182,129 | 5/1965 | Clark et al. . | |
| 3,949,388 | 4/1976 | Fuller | 128/903 X |
| 4,248,241 | 2/1981 | Tacchi | 128/715 X |
| 4,304,240 | 12/1981 | Perlin . | |
| 4,484,583 | 11/1984 | Graham . | |
| 4,619,268 | 10/1086 | Uphold et al. | 128/715 X |
| 4,686,998 | 8/1987 | Robbins . | |
| 4,705,048 | 11/1987 | Pfohl | 128/715 |
| 4,723,555 | 2/1988 | Shue | 128/715 |
| 4,777,961 | 10/1988 | Saltzman | 128/715 |

Primary Examiner—Max Hindenburg
Assistant Examiner—John P. Lacyk

Attorney, Agent, or Firm—Killworth, Gottman, Hagan & Schaeff

[57] ABSTRACT

A self-contained stethoscope transmitter comprises a pickup head including a housing which defines a precordial dome formed thereinto for contact with a patient whose bodily sounds are to be observed and/or monitored, and electronic circuitry positioned within the housing for receiving the sounds, converting the sounds into an FM signal representative thereof and transmitting the FM signal. The frequency of transmission is tunable over a range of frequencies by using a screwdriver which is removably secured within the housing. The pickup head includes a luer taper within a base of the head for alternate operation with an esophageal probe. The base can also be rotated relative to the remainder of the head to configure the head for either precordial or esophageal use with rotation of the head switching an internal battery to conserve the battery for shipment, storage or extended usage of the transmitter if desired. Preferably, the pickup head is constructed of inexpensive materials such that the stethoscope transmitter can be thrown away after a single use without concern for contamination which would otherwise require cleaning and sterilization of the stethoscope transmitter for subsequent use.

16 Claims, 3 Drawing Sheets

SELF-CONTAINED STETHOSCOPE TRANSMITTER

BACKGROUND OF THE INVENTION

The present invention relates generally to electronic stethoscopes and, more particularly, to a wireless electronic stethoscope transmitter which is included within a stethoscope pickup head.

The stethoscope has been an important medical instrument for many years and its continuing importance to the medical profession is apparent from its commonplace appearance around medical facilities. While less visible to the layman, the stethoscope is vital to the functioning of the modern operating theater since an anesthetist must often rely on auditory monitoring of a patient due to the visual obstructions caused by sterile drapes, equipment and other attending medical personnel. Auditory monitoring is performed by a sound pickup placed on the chest wall (precordial) or placed in the esophagus (esophageal) directly behind the trachea.

Of course the stethoscope has been improved over the years and many variations have been provided. For example, in the most common form of stethoscope, body sounds are transmitted through a hollow tube to the ears of treating personnel. Such instruments create clear problems, particularly within an operating theater, since the direct physical connection between the patient and treating personnel severely limits the mobility of the treating personnel. In the case of an anesthetist, such mobility is crucial to permit performance of this vital function.

To overcome movement restriction problems of the standard stethoscope, various electronic stethoscopes have been developed. In these instruments, the bodily sounds received by the stethoscope are converted into electrical signals which are then transmitted to a receiver where the signals are demodulated and monitored either directly by medical personnel or by means of electronic equipment designed to generate alarms in response to defined criteria, such as heart or breath rate. Unfortunately, currently available electronic stethoscopes are constructed as sensor units which are in turn connected to separate transmitters. The available sensor/transmitter arrangements are bulky, cumbersome, occupy valuable space which may be needed by assisting medical personnel, and may be difficult to connect and/or use. Additionally, the transmitters are sufficiently expensive that they preferably are not used as "throw-away" or disposable units but must be cleaned and sterilized for subsequent use.

Accordingly, there is a need for a self-contained stethoscope transmitter which occupies substantially no more space that existing pickup heads and does not require a separate transmitter or any interconnection to a separate transmitter. Such a self-contained stethoscope transmitter would preferably be sufficiently sturdy that it could be used over a substantial period of time, yet be constructed of inexpensive materials such that its cost would permit "throw-away" or disposable use of the transmitters if desireable or expedient, as in an operating theater.

SUMMARY OF THE INVENTION

This need is met by the self-contained stethoscope transmitter of the present invention wherein an FM transmitter is housed within a pickup head for a wireless stethoscope. The pickup head is configured to be used directly as a precordial stethoscope pickup and also to accommodate attachment of an esophageal probe to the head. To ensure that sounds are not cross-coupled, the pickup head is switchable to pass sounds either from a precordial port or from an esophageal port to a microphone of electronic circuitry of the transmitter. In switching the pickup head between the precordial and esophageal ports of the pickup head, an intermediate position is provided to disconnect an internal battery such that power to the electronic circuitry of the transmitter can be turned off when the stethoscope transmitter is not in use. The stethoscope transmitter pickup housing is preferably formed of molded plastic such that the transmitter is sufficiently inexpensive that it can be used on a throw-away or disposable basis; however, the housing is durable and formed to have a closure member which can be opened such that the internal battery can be replaced as needed for extended use, if desired. For extended use, a rechargeable battery may be provided with charging contacts on the pickup housing such that the battery can be recharged whenever the stethoscope transmitter is not in use or one unit could be charging while another unit is in use.

In accordance with one aspect of the present invention, a self-contained stethoscope transmitter comprises a pickup head including a housing which defines a precordial dome formed thereinto for contact with a patient whose bodily sounds are to be observed and/or monitored, and electronic circuit means positioned within the housing for receiving the sounds, converting the sounds into a modulated signal representative thereof and transmitting the modulated signal. Preferably, the pickup head is constructed of inexpensive materials whereby the stethoscope transmitter can be thrown away after a single use without concern for contamination which would otherwise require cleaning and sterilization of the stethoscope transmitter for subsequent use.

The electronic circuit comprises microphone means, preferably an electret microphone, for receiving the bodily sounds and the pickup head includes an opening extending through the precordial dome in alignment with the microphone means. In the illustrated embodiment, the modulated signal is a frequency modulated (FM) signal and the electronic circuit means comprises a transmission antenna extending outside the housing. To permit convenient adaptation of the transmitter for use at various locations, the circuit means preferably comprises tuner means for tuning the FM signal to a desired frequency which is not used at the location. Selective tuning of the frequency of the FM signal ensures interference free operation of the self-contained stethoscope transmitter. When tuner means are provided, the transmitter preferably further comprises tool means, such as a plastic screwdriver, for operating the tuner means with the tool means being removably secured to the housing and positioned to block access to the tuner means when stored in the housing.

To enhance the versatility of the self-contained stethoscope transmitter of the present invention, the housing includes means for coupling an esophageal probe thereto for detecting bodily sounds by means of the esophageal probe and selector means for configuring the housing to observe and/or monitor bodily sounds via the precordial dome or an esophageal probe as selected. This adaptability of the transmitter is particularly important for use in an operating theater since it permits a single design to be readily adapted for the type monitoring required for a specific surgical procedure thus reducing inventory requirements and hence expense.

The electronic circuit may comprise microphone means for receiving the bodily sounds and the esophageal probe coupling means may comprise a luer taper formed into the housing and a passage formed within the housing in communication with the luer taper. For this configuration, the pickup head includes a first opening extending through the precordial dome and the selector means comprises orienting means for selectively aligning the first opening or the passage with the microphone means to selectively observe and/or monitor sounds originating within the precordial dome or an esophageal probe connected to the luer taper.

To conserve power for shipment, storage and extended usage of the transmitter, the circuit means preferably comprises electrical switch means for selectively providing power to the circuit means when the orienting means is positioned to align the first opening or the passage with the microphone means but otherwise not providing power to the circuit means. To this end, the housing may comprise a closed cylindrical chamber and a cylindrical base rotatably mounted thereto, the precordial dome and the luer taper being formed into the base and the orienting means comprising a cam and intermating notches formed in the closed cylindrical chamber and the base. The base further defines electrical switch operating cam means positioned adjacent to the electrical switch means for operating the electrical switch means as the base and the chamber are rotated relative to one another. To facilitate use of the transmitter, the base and the chamber may comprise indicator means for indicating the relative positioning of the base to the chamber and thereby the orientation of the passage and the opening relative to the microphone means and the state of the electrical switch means.

For extended use of the transmitter, for example in use in a doctor's office or the like, the chamber may comprise a first cylindrical member and a second closure member removably secured to the first member, the circuit means comprising a circuit board mounted within the first cylindrical member and including an interchangeable battery which can be accessed for replacement by opening the second closure member.

It is thus an object of the present invention to provide a compact, self-contained stethoscope transmitter which occupies substantially no more space that existing pickup heads; to provide a compact, self-contained stethoscope transmitter which is sufficiently sturdy that it can be used over a substantial period of time, yet is sufficiently inexpensive that it can be used as a "throwaway" or disposable unit; to provide a compact, self-contained stethoscope transmitter which can directly monitor bodily sounds precordially and also receive an esophageal probe for esophageal monitoring; and, to provide a compact, self-contained stethoscope transmitter which can be conveniently switched between precordial and esophageal monitoring modes.

Other objects and advantages of the invention will be apparent from the following description, the accompanying drawings and the appended claims.

BRIEF DESCRIPTION OF THE DRAWINGS

FIG. 6 shows an inexpensive switch for one time activation of a self-contained stethoscope transmitter intended for disposable use.

DETAILED DESCRIPTION OF THE INVENTION

Figure 1:
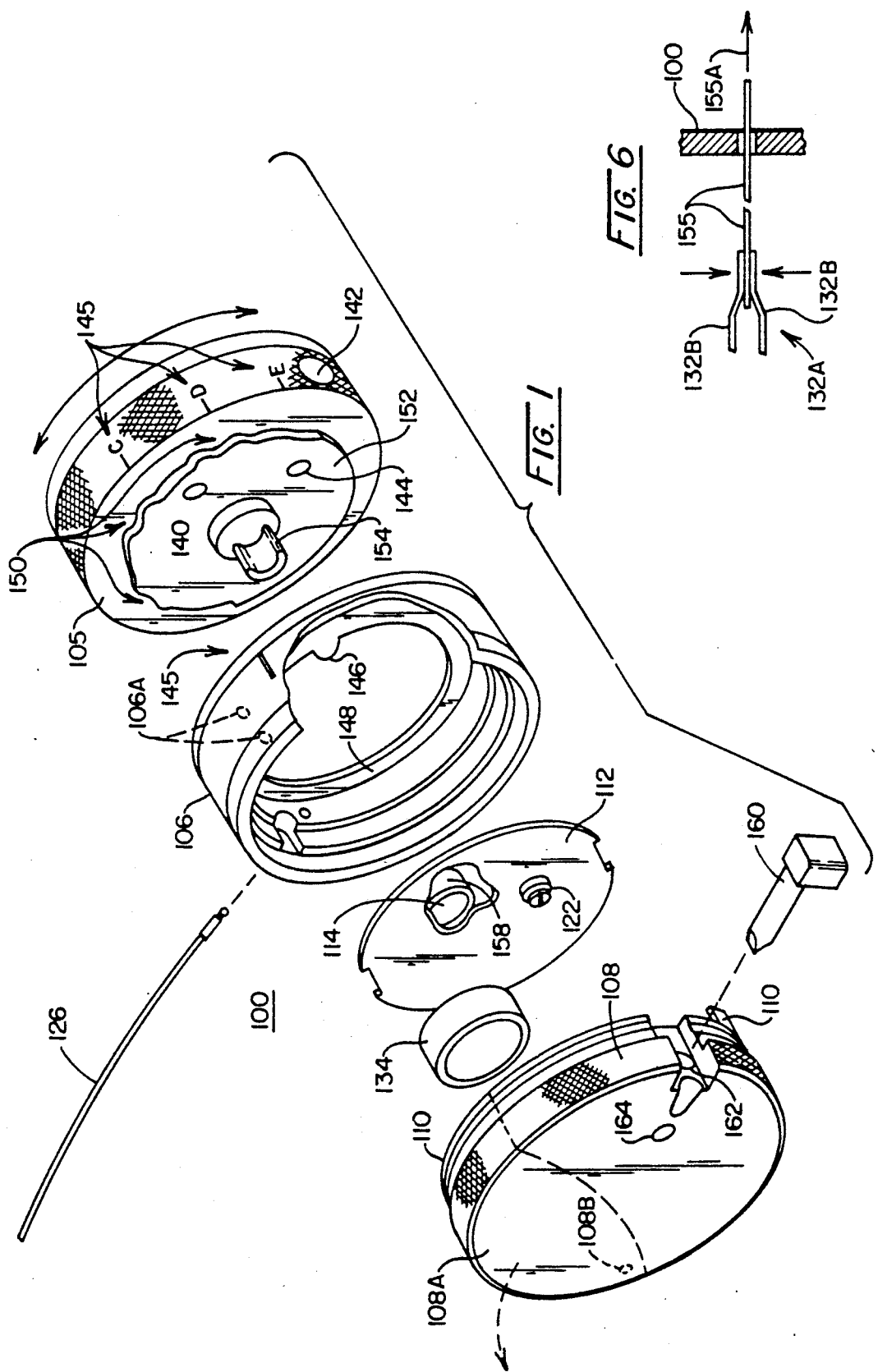
FIG. 1 is an exploded perspective view of a preferred embodiment of a self-contained stethoscope transmitter of the present invention.
Figure 2:
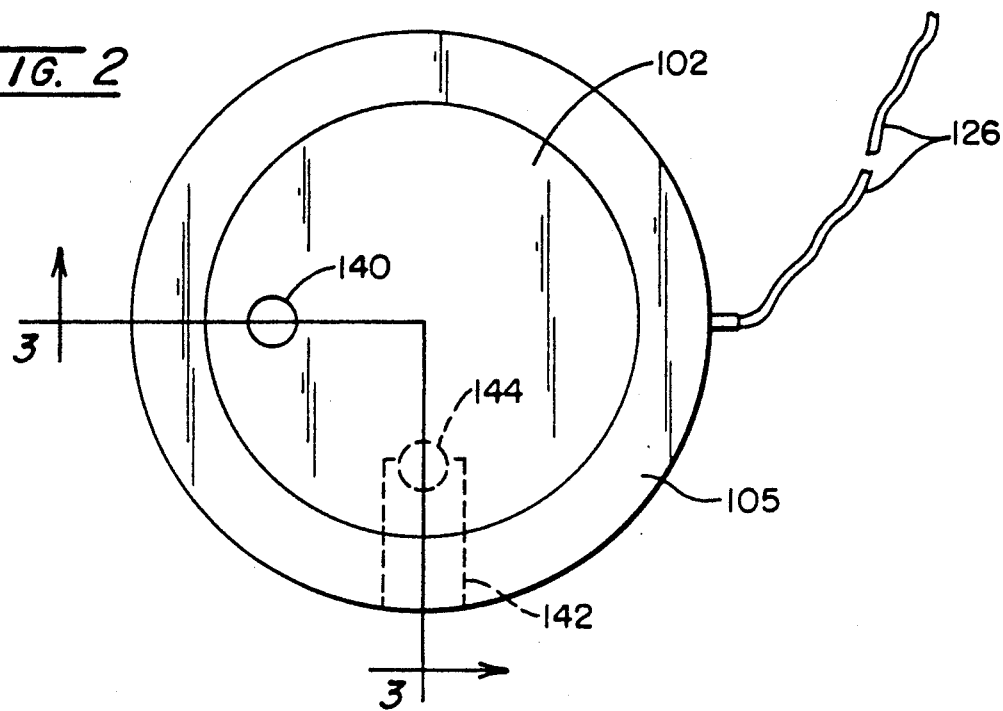
FIG. 2 is back view of the self-contained stethoscope transmitter of FIG. 1 looking into a precordial dome of the transmitter.

Reference is now made to the drawing figures wherein a self-contained stethoscope transmitter in accordance with the present invention is shown in exploded perspective view in FIG. 1. The transmitter takes the form of a stethoscope pickup head 100 including a housing which defines a precordial dome 102, best shown in FIGS. 2 and 3, for contact with a patient (not shown) whose bodily sounds are to be observed and/or monitored. The housing comprises a generally cylindrical chamber 104 which is closed on one end by a rotatably mounted, generally cylindrical base 105 which includes the precordial dome 102. The chamber 104 is defined by a generally cylindrical first member 106 and a second closure member 108 which is removably secured to the first member 106, for example by ribbed extensions 110 or otherwise.

Figure 5:
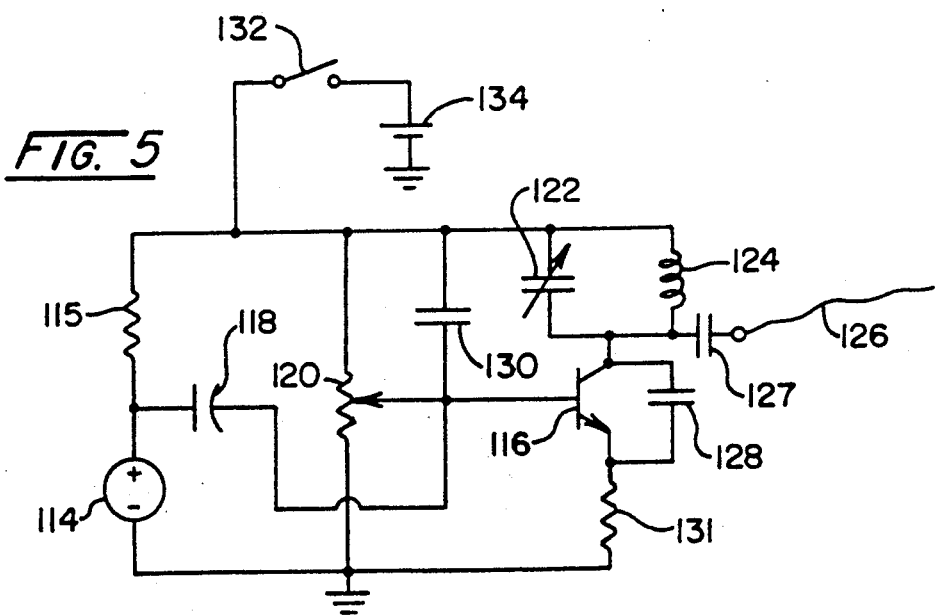
FIG. 5 is a schematic circuit diagram of electronic circuitry usable in the self-contained stethoscope transmitter of the present invention.

Electronic circuit means, shown in electrical schematic form in FIG. 5, comprises a circuit board 112 positioned within the housing and, more particularly, mounted within the first member 106 thereof for receiving bodily sounds, converting the sounds into a modulated signal representative of the sounds and transmitting the modulated signal. Referring to FIG. 5, an electronic circuit which can be used in the present invention comprises microphone means taking the form of an electret microphone 114 whose load current is determined by a resistor 115. The microphone 114 detects bodily sounds which are to be monitored using the transmitter. The electrical signals generated by the microphone 114 in response to bodily sounds are coupled to the base of a transistor 116 by a capacitor 118, with bias current being provided to the transistor 116 by a potentiometer 120 which permits the transistor bias to be adjusted.

The transistor 116 in combination with a tank circuit defined by a trimmer capacitor 122 and an inductor 124 form a tuned Hartley oscillator circuit which generates a frequency modulated (FM) signal representative of the bodily sounds received by the microphone 114. The FM signal is transmitted by a transmission antenna 126 coupled to the collector of the transistor 116 by a capacitor 127. The transmission antenna 126 may be permanently connected to the circuit or removably coupled, as shown, such that the antenna 126 can be replaced if damaged. The carrier frequency of the FM signal is determined by adjustment of the trimmer capacitor 122. A capacitor 128 provides positive feedback from the tank circuit to the emitter of the transistor 116 and a capacitor 130 provides feedback to the base of the transistor 116 to sustain oscillation. A resistor 131 serves as a load resistor for the transistor 116 and electrical switch means taking the form of a switch 132 provides for selectively connecting power from an interchangeable battery 134 to the circuit.

Preferably, the pickup head 100 is constructed of inexpensive materials such as polypropylene, nylon or other appropriate materials such that the stethoscope transmitter can be thrown away after a single use without concern for contamination which would otherwise require cleaning and sterilization of the stethoscope transmitter for subsequent use. Disposable use may be preferred, for example, in an operating theater. For extended use, the closure member 108 can be removed to permit replacement of the battery 134. Alternately, the closure member 108 may be fixedly secured to the first member 106 and include a battery access door 108A which may be pivotally mounted to the closure member 108, for example about a pivot pin 108B, or otherwise mounted to permit the closure member 108 to be opened for access to the battery 134, see FIG. 1. Another alternative for extended operation is for a rechargeable battery to be used. For rechargeable use, battery charger access contacts are provided on the housing, such as contacts 106A, with one of the contacts 106A being axially centrally located and the other axially offset therefrom to ensure that only charging current of the proper polarity is provided.

For use of the transmitter for precordial observation and/or monitoring, the precordial dome 102 is appropriately positioned on a patient. The pickup head 100 and more particularly the precordial dome 102 formed into the base 105 includes an opening 140 extending therethrough with the opening 140 being aligned with the microphone 114 for precordial use. The housing of the pickup head 100 includes means for coupling an esophageal probe to the housing for detecting bodily sounds via the esophageal probe. The esophageal coupling means takes the form of a luer taper 142 and a passage 144 in communication with the luer taper 142, both the luer taper 142 and the passage 144 being formed into the base 105.

Selector means for configuring the housing to observe and/or monitor bodily sounds via either the precordial dome 102 or an esophageal probe connected to the luer taper 142 are provided by rotatably mounting the base 105 to the first member 106 of the housing. In this way, the base 105 and the remainder of the housing can be rotated relative to one another such that either the opening 140 or the passage 144 is aligned with and transfers sounds to the microphone 114. Indicator means comprising markings 145 on the base 105 and the first member 106 permit convenient configuration of the transmitter for a desired mode of operation. The markings 145 show the orientation of the base 105 to the first member 106 by indicating the alignment of the opening 140 with the microphone 114 (C=Chest for precordial operation), the alignment of the passage 144 with the microphone 114 (E=Esophageal for esophageal operation) or alignment of neither (O=Open for misalignment and opening of the power switch 132).

Figure 3:
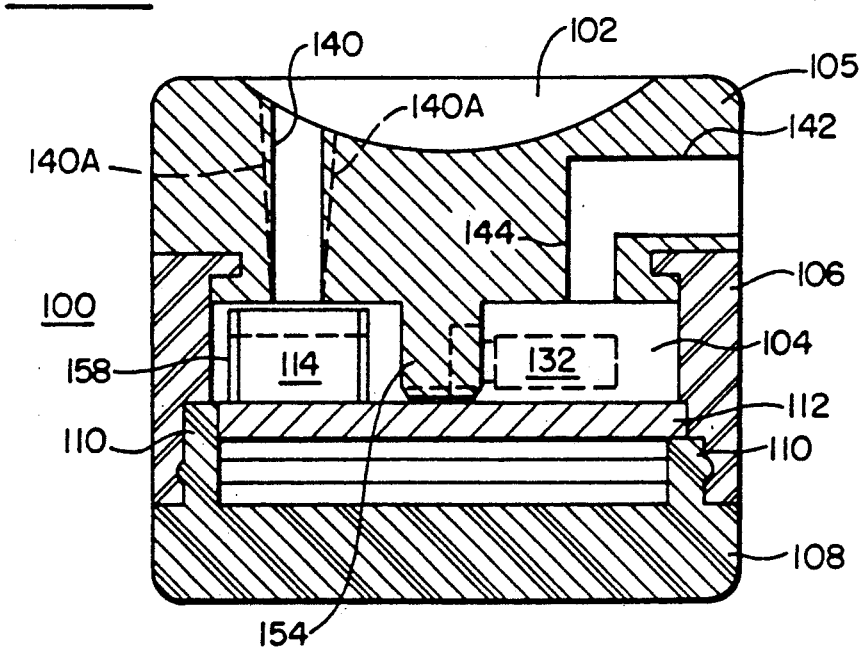
FIG. 3 is a sectional view of the self-contained stethoscope transmitter of the present invention taken along the section line 3—3 of FIG. 2.
Figure 4:
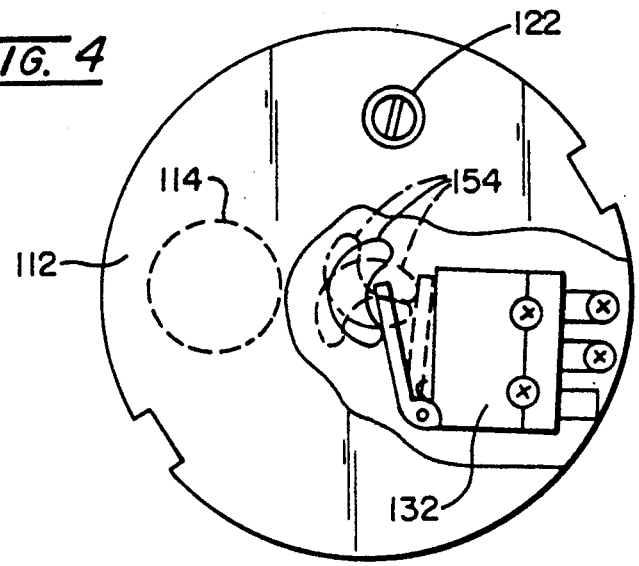
FIG. 4 is a partially broken-away front view of the circuit board of FIG. 1 showing operation of an electrical switch mounted thereon.

The markings 145 are aligned to correspond to a cam 146 formed on a retaining ring 148 of the member 106 for retaining the base 105 thereto and notches 150 on the base 105. The cam 146 is received by and intermates with the notches 150 formed into a flange 152 on the base 105 to define the preferred three positions of the base 105 relative to the remainder of the housing. Rotation of the base 105 also controls operation of the switch 132 by means of electrical switch operating cam means taking the form of a crescent shaped cam 154 in the illustrated embodiment. The orientation and positioning of the cam 154 relative to the switch 132 is best shown in FIGS. 3 and 4. As shown in FIG. 4, when the base 105 is positioned relative to the remainder of the housing such that the markings 145 indicate Open "O", the switch 132 remains unoperated and hence open such that the battery 134 is not electrically connected to the remainder of the circuit shown in FIG. 5. However, when the base 105 is rotated such that the markings 145 indicate Chest "C" or Esophageal "E", the battery 134 is electrically connected to the remainder of the circuit to activate the transmitter.

For a disposable stethoscope transmitter, the design could be substantially simplified if desired. For example, a one time power activating switch 132A could be provided by a pair of normally closed contacts 132B which are initially separated from one another by a sheet 155 of insulating material which extends beyond the pickup head 100. When the transmitter was to be placed into service, the sheet 155 would be pulled from the transmitter as shown by an arrow 155A to permit the contacts 132B to close and thereby activate the transmitter. Another simplification for the present invention, where possible, is to form the opening 140 as a luer taper 140A such that there is but one port for both precordial and esophageal access.

To help prevent cross-coupling between the precordial port defined by the opening 140 and the esophageal port defined by the luer taper 142 and the communicating passage 144, a cylindrical sleeve 158 may be provided around the microphone 114 as shown in FIGS. 1 and 3. For additional sound deadening, if required, the entire chamber 104 may be filled with a foamed insert with an opening therethrough which substantially corresponds the sleeve 158. To be sure that the transmitter can always be conveniently tuned or retuned as needed, preferably tool means taking the form of a screwdriver 160 is provided and removably secured to the housing. As shown in FIG. 1, the screwdriver 160 is aligned for insertion into its storage compartment 162 in the second closure member 108. When fully inserted into its storage compartment 162, it blocks access to the trimmer capacitor 122 which serves as tuner means for selecting the operating carrier frequency of the transmitter. For tuning the transmitter, the screwdriver 160 is removed from its storage compartment 162 and is inserted through tuner port 164 which is opened by removal of the screwdriver 160.

The transmitter of the present invention is preferably operated with an existing FM radio receiver such as one of the compact, portable receivers which are commonly seen in use by joggers. Of course, a separate or special FM receiver could be provided for use with the present invention. Since available FM frequencies vary from location to location, the transmitters and receivers should have the capability of being tuned. This is true even though the transmitters (and receivers, if provided) are initially tuned to an FM frequency which is available for the location to which they are shipped because shipments can be diverted and transmitters can easily be carried from one location to another.

While the transmitters can be provided in any convenient package form, it may be preferred to package transmitters in individual sealed sterile packages. Such packaging may particularly be preferred for transmitters which are intended for use in an operating theater. While use of the transmitters of the present invention should be apparent from the above description, their use will now be briefly described for use in an operating theater.

An anesthetist or other member of a surgical team would obtain one or a number of pretuned transmitters in sterile packages. The package(s) would be opened and the transmitter(s) turned to the desired operating mode (precordial "C" or esophageal "E"). Presetting the transmitter(s) to the desired operating mode would also activate the transmitter(s) circuitry and permit preoperation testing. Of course, if more than one transmitter is to be used the transmitters must be tuned to differing available FM frequencies. If the transmitter(s) were not for this specific location or more than one is used, the transmitter(s) would be conveniently tuned or retuned by means of the sterile tuning tool provided with each transmitter.

Use of these transmitters permits anyone with an appropriately tuned FM receiver to listen in on the patient being monitored provided they are within the transmission range of the transmitters (approximately 10–15 feet) such that the transmitters permit free movement of personnel monitoring the patient and also provide for multiple monitoring which may be desireable for example in a teaching hospital. These transmitters also facilitate continuous monitoring of a trauma victim. For such usage, a stethoscope transmitter can be secured to the patient by the personnel providing initial treatment, with the transmitter providing continuing monitoring signals as the patient is transported, treated in an emergency room, transferred to an intensive care unit or along whatever path of treatment the patient may travel.

After use, the transmitter(s) can be thrown away to ensure that any contamination is not spread beyond the operating theater. Alternately, if appropriate under the circumstances, the transmitter(s) can be retained for later use. If repeated use leads to drainage of the operating battery, the battery can be conveniently replaced or recharged.

Having thus described the self-contained stethoscope transmitter of the present invention in detail and by reference to preferred embodiments thereof, it will be apparent that modifications and variations are possible without departing from the scope of the invention defined in the appended claims.

What is claimed is:

1. A self-contained stethoscope transmitter comprising:
   a pickup head including a housing which defines a precordial dome for contact with a patient whose bodily sounds are to be observed and/or monitored, said housing comprising a closed chamber and a base movably mounted thereto and including means for coupling an esophageal probe to said housing for detecting bodily sounds by means of said esophageal probe and selector means for moving said base relative to said closed chamber such that said housing is configured to observe and/or monitor bodily sounds via said precordial dome or an esophageal probe; and
   electronic circuit means positioned within said housing for receiving said sounds, converting said sounds into a modulated signal representative thereof and transmitting said modulated signal.

2. A self-contained stethoscope transmitter as claimed in claim 1 wherein said pickup head is constructed of inexpensive materials whereby said stethoscope transmitter can be thrown away after a single use without concern for contamination which would otherwise require cleaning and sterilization of the stethoscope transmitter for subsequent use.

3. A self-contained stethoscope transmitter as claimed in claim 1 wherein said electronic circuit means comprises microphone means for receiving said bodily sounds and said pickup head includes an opening extending through said precordial dome in alignment with said microphone means.

4. A self-contained stethoscope transmitter as claimed in claim 3 wherein said opening is formed as a luer taper to receive an esophageal probe.

5. A self-contained stethoscope transmitter as claimed in claim 3 wherein said microphone means is an electret microphone.

6. A self-contained stethoscope transmitter as claimed in claim 1 wherein said electronic circuit means comprises microphone means for receiving said bodily sounds and said esophageal probe coupling means comprises a luer taper formed into said housing and a passage formed within said housing in communication with said luer taper, said pickup head including a first opening extending through said precordial dome and said selector means comprising orienting means for selectively aligning said first opening or said passage with said microphone means to selectively observe and/or monitor sounds originating within said precordial dome or an esophageal probe connected to said luer taper.

7. A self-contained stethoscope transmitter as claimed in claim 6 wherein said circuit means comprises electrical switch means for selectively connecting power to said circuit means when said orienting means is positioned to align said first opening or said passage with said microphone means.

8. A self-contained stethoscope transmitter as claimed in claim 7 wherein said housing comprises a closed generally cylindrical chamber and a generally cylindrical base rotatably mounted thereto, said precordial dome and said luer taper being formed into said base and said orienting means comprising a cam and intermating notches formed in said closed cylindrical chamber and said base.

9. A self-contained stethoscope transmitter as claimed in claim 8 wherein said base further defines electrical switch operating cam means positioned adjacent to said electrical switch means for operating said electrical switch means as said base and said chamber are rotated relative to one another.

10. A self-contained stethoscope transmitter as claimed in claim 9 wherein said base and said chamber comprise indicator means for indicating the relative positioning of said base to said chamber and thereby the orientation of said passage and said opening relative to said microphone means and the state of said electrical switch means.

11. A self-contained stethoscope transmitter as claimed in claim 10 wherein said chamber comprises a generally cylindrical first member and a second closure member secured to said first member, said circuit means comprising a circuit board mounted within said first cylindrical member and including an interchangeable battery which can be accessed for replacement by opening said second closure member.

12. A self-contained stethoscope transmitter as claimed in claim 11 wherein said microphone means is an electret microphone.

13. A self-contained stethoscope transmitter as claimed in claim 1 wherein said electronic circuit means comprises a rechargeable battery and said pickup head includes charging contacts connected to said battery.

14. A self-contained stethoscope transmitter as claimed in claim 1 wherein said electronic circuit means comprises an antenna which is detachably connected thereto to permit replacement of said antenna.

15. A self-contained stethoscope transmitter comprising:

a pickup head including a housing which defines a precordial dome for contact with a patient whose bodily sounds are to be observed and/or monitored;

electronic circuit means positioned within said housing for receiving said sounds, converting said sounds into a frequency modulated signal representative thereof and transmitting said frequency modulated signal, said electronic circuit means comprising a transmission antenna and tuner means for tuning said frequency modulated signal to a desired frequency to ensure interference free operation of said self-contained stethoscope transmitter; and tool means for operating said tuner means, said tool means being removably secured to said housing and positioned to block access to said tuner means when secured to said housing.

16. A self-contained stethoscope transmitter comprising:

a pickup head including a housing which defines a precordial dome for contact with a patient whose bodily sounds are to be observed and/or monitored, said pickup head being constructed of inexpensive materials whereby said stethoscope transmitter can be thrown away after a single use without concern for contamination which would otherwise require cleaning and sterilization of the stethoscope transmitter for subsequent use; and electronic circuit means positioned within said housing for receiving said sounds, converting said sounds into a modulated signal representative thereof and transmitting said modulated signal, said circuit means including one time transmitter activating switch means comprising a pair of normally closed contacts and an electrically insulating sheet inserted therebetween to open said contacts, said sheet extending through said pickup head and being pulled to remove said sheet and close said contacts to activate said transmitter.

* * * * *